United States Patent
Den Ridder et al.

(10) Patent No.: US 10,428,000 B2
(45) Date of Patent: Oct. 1, 2019

(54) DIVIDING WALL IN ETHANOL PRODUCTION PROCESS

(71) Applicant: Cargill, Incorporated, Wayzata, MN (US)

(72) Inventors: Johannes Jacobus Joseph Den Ridder, Huijbergen (NL); Josephus Johannes Petrus Maria Goorden, Roosendaal (NL); Didier Agnes Joseph Koster, Womelgem (BE)

(73) Assignee: CARGILL, INCORPORATED, Wayzata, MN (US)

( * ) Notice: Subject to any disclaimer, the term of this patent is extended or adjusted under 35 U.S.C. 154(b) by 215 days.

(21) Appl. No.: 14/900,287

(22) PCT Filed: Jun. 20, 2014

(86) PCT No.: PCT/US2014/043379
§ 371 (c)(1),
(2) Date: Dec. 21, 2015

(87) PCT Pub. No.: WO2014/205332
PCT Pub. Date: Dec. 24, 2014

(65) Prior Publication Data
US 2016/0368845 A1    Dec. 22, 2016

(30) Foreign Application Priority Data

Jun. 21, 2013   (EP) .................................. 13003173

(51) Int. Cl.
*C07C 29/80* (2006.01)
*B01D 3/14* (2006.01)
*B01D 3/00* (2006.01)

(52) U.S. Cl.
CPC .............. *C07C 29/80* (2013.01); *B01D 3/005* (2013.01); *B01D 3/141* (2013.01)

(58) Field of Classification Search
CPC .......... B01D 3/005; B01D 3/141; C07C 29/80
See application file for complete search history.

(56) References Cited

U.S. PATENT DOCUMENTS

| | | | | |
|---|---|---|---|---|
| 2,290,442 A * | 7/1942 | Metzl | ..................... | B01D 3/001 203/55 |
| 4,496,430 A * | 1/1985 | Jenkins | .................... | B01D 3/22 196/111 |
| 6,551,465 B1 * | 4/2003 | Van Zile | .................. | B01D 3/14 159/44 |
| 6,846,389 B2 * | 1/2005 | Kaibel | ..................... | B01D 3/14 203/1 |
| 2005/0058746 A1 * | 3/2005 | Wheatley | ................. | C12G 3/12 426/12 |
| 2009/0299109 A1 * | 12/2009 | Gruber | ..................... | C10L 1/04 585/14 |

FOREIGN PATENT DOCUMENTS

| | | |
|---|---|---|
| RU | 2174974 C1 | 10/2001 |
| RU | 2187492 C1 | 8/2002 |
| WO | 2008/076749 A1 | 6/2008 |

OTHER PUBLICATIONS

Difford, S. (2011). Distillation—The science of distillation. Accessed Nov. 7, 2017 at https://www.diffordsguide.com/encyclopedia/198/bws/distillation-the-science-of-distillation.*
Wang et al. (2011). Experiment Study of Alcohol Ternary Mixture Separation by Dividing Wall Column. Guangzhou Chem. Ind., 39(22), 42-45.*
PTO 126596 (English translation of Wang et al.) Received Oct. 25, 2017.*
Difford, S. (2011). Distillation—The science of distillation. Accessed Nov. 7, 2017 at https://www.diffordsguide.com/encyclopedia/198/bws/distillation-the-science-of-distillation (Year: 2011).*
Wang et al. (2011). Experiment Study of Alcohol Ternary Mixture Separation by Dividing Wall Column. Guangzhou Chem. Ind., 39(22), 42-45. (Year: 2011).*
Wang_2011_ENG (USPTO English translation of Wang) (Year: 2011).*
Wang et al. (Experiment Study of Alcohol Ternary Mixture Separation by Dividing Wall Column. Guangzhou Chem. Ind., 39(22), 42-45). Translation by USPTO. (Year: 2011).*
Jinglan Gao et al.: "Avoiding the Black-Hole Problem by the Arrangements of Multiple Intermediate Products to Dividing-Wall Distillation Columns", Industrial & Engineering Chemistry Research, vol. 52. Feb. 28, 2013, pp. 4178-4201, XP002715162, ISSN: 0688-5885.
Ömer Yildirim et al.: "Dividing wall columns in chemical process industry: A review on current activities", Seperation and Purification Technology, vol. 80, May 26, 2011, pp. 403-417, XP002715161, ISSN:1383-5866.
R. Premkumar et al.:"Retrofitting conventional column systems to dividing-Wall Columns", Chemical Engineering Research and Design, vol. 87, 2009, pp. 47-60, XP002715163, ISSN:0263-8762.

* cited by examiner

*Primary Examiner* — Youngsul Jeong
*Assistant Examiner* — Gabriel E Gitman

(57) ABSTRACT

The invention relates to a process for the purification of ethanol wherein a dividing wall column is used. In particular, the invention relates to a process for the purification of a feed stream comprising ethanol and impurities such as higher alcohols. The invention further relates to the use of dividing wall in distillation column in an ethanol purification process.

11 Claims, No Drawings

DIVIDING WALL IN ETHANOL PRODUCTION PROCESS

CROSS REFERENCE TO RELATED APPLICATIONS

This application is a national phase entry of International Application No. PCT/US14/043379, filed Jun. 20, 2014, entitled "DIVIDING WALL IN ETHANOL PRODUCTION PROCESS", which claims priority to European Patent Application, Ser. No. 13003173.5, filed Jun. 21, 2013, entitled "DIVIDING WALL IN ETHANOL PRODUCTION PROCESS", which are hereby incorporated by reference in their entirety.

FIELD OF THE INVENTION

The invention relates to a process for the purification of ethanol comprising the use of dividing wall column. In particular, the invention relates to a process for the purification of a feed stream comprising ethanol and impurities such as higher alcohols. In particular the invention relates to an improved separation of ethanol and impurities such as higher alcohols.

BACKGROUND OF THE INVENTION

Ethanol is a 2-carbon alcohol with the molecular formula $CH_3CH_2OH$. It is an important industrial product nowadays and its importance is increasing. Ethanol can be produced by a chemical process or via biological processes, typically by yeast fermentation out of a suitable substrate.

Ethanol finds different industrial applications. It is largely used in the food and beverage industry. This ethanol (potable ethanol) needs to meet high quality standards in terms of purity. Purification steps are thus an important part of the production process of potable ethanol. Potable ethanol but also less purified ethanol is also used in pharmaceutical applications. Further, ethanol is increasingly used as an alternative energy source for fossil fuels. This ethanol is referred to as fuel ethanol, bio-ethanol or biofuel. It is less purified than potable ethanol but the production process is largely similar and purification steps, although operated to a lesser extent than in potable ethanol process, remain an important part of the process.

There is an ever existing need from industry of a process with reduced energy consumption, reduced complexity and with lower investment costs and/or higher yield. The present invention provides for such a solution.

SUMMARY OF THE INVENTION

The present invention relates to a process for the purification of ethanol comprising the steps of:
  a. Distilling in a distillation column, a feed stream comprising ethanol and impurities, such as one or more higher alcohols, and
  b. Collecting a product stream having a higher purity in ethanol compared to the feed stream,
characterised in that the distillation column comprises at least one dividing wall.

Further, the present invention relates to a use of dividing wall in a distillation column in an ethanol purification process.

DETAILED DESCRIPTION

The term "about", as used herein when referring to a measurable value is meant to encompass variations of 5%, 4%, 3%, 2%, 0.5% or even 0.1% of the specified value.

The present invention relates to a process for the purification of ethanol comprising the steps of:
  a. Distilling in a distillation column, a feed stream comprising ethanol and impurities, such as one or more higher alcohols, and
  b. Collecting a product stream having a higher purity in ethanol compared to the feed stream,
characterised in that the distillation column comprises at least one dividing wall.

Thus the present invention relates to a process for the purification of ethanol from a feed stream comprising the steps of:
  c. Distilling in a distillation column, the feed stream comprising ethanol and impurities, such as one or more higher alcohols, and
  d. Collecting a product stream having a higher purity in ethanol compared to the feed stream,
characterised in that the distillation column comprises at least one dividing wall.

Preferably, the feed stream comprises at least 5 volume % (v %) of ethanol, based on the volume of the feed stream. Preferably, the feed stream comprises from 8 to 50 v %, more preferably from 10 to 45 v %, even more preferably from 10 to 40 v %, yet even more preferably from 10 to 30 v %, yet even more preferably from 12 to 20 v %, most preferably from 15 to 18 v % of ethanol, based on the volume of the feed stream. The content in volume % is measured with a density meter, such as DMA 5000 from Anton Paar.

The process of the present invention relates to the purification of ethanol from a feed stream comprising ethanol and impurities such as one or more higher alcohols. The process comprises collecting a product stream having a higher purity in ethanol compared to the feed stream. Said product stream has a purity in ethanol of from 60 to 98 v %, more preferably from 70 to 96 v %, even more preferably from 80 to 96 v %, yet even more preferably from 90 to 96 v %. About 96 v % ethanol purity is suitable for use as potable ethanol or for use in some pharmaceutical applications. Typically collecting the product stream is done through an outlet at the higher end of the distillation column.

Preferably, the process further comprises collecting one or more streams having a higher purity in the one or more higher alcohols compared to the feed stream. The one or more higher alcohols have a lower volatility than ethanol at a given temperature and pressure and are collected typically through one or more outlet placed intermediate of the higher end and the lower end of the distillation column. The one or more streams collected can be further processed to recover ethanol still present therein. One advantage of the dividing wall in the distillation column is that less ethanol remains in said collected streams in comparison to a process where no dividing wall is present in the distillation column. Thus with the process of the present invention, a higher percentage of the total ethanol present in the feed stream ends up in the product stream. It has thus surprisingly been found that a dividing wall in a distillation column improves the separation of ethanol and impurities such as higher alcohols and increases the ethanol yield of the column.

Preferably the feed stream further comprises water. Water may be present in an amount of from 5 to 95 v %, from 10 to 90 v %, from 15 to 85 v %, from 20 to 80 v %, from 30 to 70 v %, from 40 to 60 v %, from 45 to 50 v %, based on the volume of the feed stream. Thus the feed stream comprises at least three components having a different volatility at a given temperature and pressure, ethanol, having the higher volatility; impurities, such as one or more higher alcohols, having an intermediate volatility and water having a lower volatility. More preferably the feed stream is a mixture consisting essentially of ethanol, water and impurities, such as one or more higher alcohols.

Preferably, the impurities are present in the feed stream in an amount of from 1 to 25000 mg/l Absolute Alcohol (AA), more preferably from 100 to 25000 mg/l AA, even more preferably from 240 to 12000 mg/l AA, most preferably from 300 to 7000 mg/l AA.

Preferably, the impurities are one or more higher alcohols. Thus preferably, the higher alcohols are present in the feed stream in an amount of from 1 to 25000 mg/l AA, more preferably from 100 to 25000 mg/l AA, even more preferably from 240 to 12000 mg/l AA, most preferably from 300 to 7000 mg/l AA.

Said one or more higher alcohols preferably comprise propanol and/or fusel alcohols. More preferably the higher alcohols comprise both propanol and fusel alcohols. Fusel alcohols or 'fusel' or also known as 'fusel oil(s)' are defined as alcohols having a higher molecular mass than 1-propanol. Main fusel alcohols are isoamyl alcohol (IUPAC 3-methyl-1-butanol), isobutanol (IUPAC 2-methylpropan-1-ol), 1-butanol and 2-butanol.

Preferably, the feed stream comprises from 1 to 20000 mg/l AA, more preferably from 1to 10000 mg/l AA, even more preferably from 40 to 4000 mg/l AA of propanol and/or from 1to 30000 mg/l AA, more preferably from 100 to 15000 mg/l AA, even more preferably from 200 to 8000 mg/l AA of fusel alcohols. For the purpose of the present invention, the amount of higher alcohols (mg/l AA) is measured by gas chromatography (CC) and represents the amount in mg per liter of 100% pure ethanol.

More preferably, ethanol is present in an amount below its azeotropic concentration. Azeotrop mixtures of ethanol are known in the art. The azeotropic concentration of ethanol will depend on the specific azeotrope mixture. Preferably, the azeotrope is ethanol with water. Thus preferably, ethanol is present below its azeotropic concentration of the ethanol-water azeotrope.

Most preferably, the feed stream comprises from 12 to 18 v % of ethanol and from 80 to 1000 mg/l AA of propanol and from 300 to 6000 mg/l AA of fusel alcohols.

Traditional distillation is a method of separating a binary or multiple component liquid mixture based on differences in volatility of the components in the boiling liquid mixture. Besides traditional distillation other distillation methods exist like reactive, azeotropic, extractive distillation etc. and combinations of these methods. Distillation is well known and well described in the art. Distillation can be batch or continuous. Industrial distillation is usually continuous distillation and typically done in a distillation column. Preferably the distillation of the present invention is continuous distillation. Distillation results in several outlet streams: one stream, typically leaving the distillation column at the higher end, the distillate or product stream, containing the most volatile component(s) of the feed stream; and one stream, typically leaving the distillation column at the lower end, the lower or bottom stream, containing the least volatile component(s) of the feed stream. Additionally, one or more side streams can be recovered intermediate between the higher end and the lower end of the distillation column, called side streams or side draw-off streams, containing components having a volatility in between the component(s) of the product stream and the component(s) of the bottom stream. The skilled person will be able to determine the suitable distillation conditions, depending on the incoming feed stream(s) and on the desired composition of the different outlet streams. Distillation can be repeated to increase the purity of a stream from one column to the next. The distillation of the present invention comprises at least one distillation column comprising at least one dividing wall.

Dividing/divided wall columns or DWC (I.e., distillation columns provided with a dividing wall) are known in the art. They are used to separate multicomponent mixtures, mostly ternary mixtures, typically equimolar mixtures or mixtures of components present in significant amounts in said mixture. DWC is mainly applied in the chemical industry. Existing processes do not use DWC for purification purposes. Different types of dividing wall columns exist, "standard" DWC, reactive DWC, azeotropic DWC and extractive DWC and combinations. Preferably in the present invention, DWC is "standard" DWC, i.e. where separation of a multicomponent mixture is effected by feeding the mixture on one side of the wall (the feed side of the wall) and collecting one or more draw-offs on the other side of the wall, without the addition of a product to react with and/or change the volatility of the components present in the column.

Preferably the process of the present invention comprises prior to step a), the fermentation of a suitable substrate by a microorganism under suitable conditions.

The fermentation substrate can be any suitable substrate comprising a carbohydrate source and a nitrogen source useful for the microorganism responsible for the conversion of fermentable sugars into ethanol and carbon dioxide gas and by-products.

Suitable fermentation conditions are well known to the skilled person, and will be determined in function of the substrate, the microorganism and the desired end product.

The process of the present invention is a process to produce ethanol as the end product. The ethanol can be fuel ethanol or potable ethanol, preferably the ethanol is potable ethanol.

Thus preferably, the feed stream is coming from a yeast fermentation process. During such process, besides ethanol, other products are formed and are present as impurities, such as higher alcohols. High quality ethanol however should be substantially free of impurities such as said higher alcohols, i.e. the impurities should be present below the detection limit of suitable analytical equipment such as Gas Chromatography for example. It is therefore an important part of an ethanol production process by yeast fermentation to purify the ethanol by separating it from said impurities in particular from higher alcohols. Typical ethanol purification process involve a first distillation to separate volatile components (comprising ethanol and higher alcohols) from the least volatile components comprised in the fermentation medium (water, yeast, organic acids, biomass, non-sugar dry matter and the like). For potable ethanol, this first distillation is usually followed by a step of washing with water and a further distillation where high quality ethanol is recovered and higher alcohols are removed in side streams (i.e. a rectification). These higher alcohols side streams still contain at least 7% of the total ethanol produced during fermentation. This ethanol, or at least part of it, needs to be recovered from the side streams by means of one or more further specific distillation columns, which increases the process complexity and cost.

It has been surprisingly found that by placing a dividing wall in the distillation column, which is preferably a rectification column, separation of ethanol from higher alcohols and preferably from water is possible and that the separation is much more efficient than when no dividing wall is used, i.e. the purity of the different higher alcohol side streams that are collected is higher and thus containing less ethanol which leaves the column via the main draw-off (product stream) where the bulk of ethanol leaves the column. In particular, by increasing the purity of the fusel draw off stream (i.e. by increasing the amount of the fusel alcohols in this stream) the present invention also allows to operate in a much easier way a heterogeneous phase separation of the fusel draw off stream in order to recover part or all of the remaining ethanol in this stream. Thereby the efficiency of the process is yet even more increased. Such heterogeneous phase separation of the fusel draw off stream is done by a washing step where water is used as washing medium. Without dividing wall, the amount of ethanol present in the side draw-off streams is at least 6 v/v % of the total ethanol present in the feed stream. By implementing the process of the present invention, the amount of ethanol present in the side draw-off streams is less than 6 v/v %, preferably less than 5 v/v %, more preferably less than 4 v/v %, even more preferably less than 3 v/v %, most preferably less than 1.5 v/v %. Thereby the amount of ethanol present in the product stream is increased by at least 1 v/v %, preferably at least 3 v/v %, more preferably by at least 5 v/v %.

Preferably the dividing wall is a wall with a height from 2 to 50%, preferably 4 to 40%, more preferably 5 to 30%, even more preferably from 10 to 20% of the total height of the distillation column. The distillation column can be a packed type column or a tray type column. Preferably the distillation column is a tray type column. These are well known in the art. Preferably, the dividing wall extends over a length of from 1 to 30, preferably 2 to 25, more preferably 4 to 20, even more preferably 5 to 15, yet even more preferably 10 to 15 trays. The shape of the wall can be any suitable shape described in the art, such as a straight wall, a wall bent in a Z or U shape, a straight wall having one or both ends with a different orientation.

The dividing wall divides the distillation column in two connecting areas, a feed side (the side of the wall where the feed stream enters the column) and the other side, the outlet side (the side of the wall where the draw off streams exit the column). Preferably, propanol building up on the feed side of the dividing wall is collected and fed, for example with a pump, back into the distillation column at the outlet side of the dividing wall. Thus preferably the distillation column comprising the dividing wall comprises a means for collecting propanol building up on the feed side of the dividing wall and feeding said propanol into the column at the other side of the dividing wall. This set up increases further the built up of propanol, thus increases the purity of the propanol draw off stream, and further increases the ethanol yield of the column. The fusel alcohols building up at the feed side of the dividing wall can also be collected and fed, for example with a pump, back into the distillation column at the outlet side of the dividing wall. This set up increases further the built up of fusel alcohols, thus increases the purity of the fusel draw off stream, and further increases the ethanol yield of the column. Thus preferably, the distillation column comprising the dividing wall comprises a means for collecting the fusel building up on the feed side of the dividing wall and feeding said fusel into the column at the other side of the dividing wall.

In a preferred embodiment, the present invention relates to a process for the production of ethanol comprising:
  a) Fermenting a substrate by yeast to produce a fermented medium comprising ethanol,
  b) Separating a stream comprising from 5 to 25 v % ethanol from the rest of the fermented medium by means of a first distillation column,
  c) Diluting with water the stream obtained in step b) to obtain a stream comprising from 12 to 18 v % of ethanol,
  d) Distilling the stream of step c) by means of a further distillation column, i.e. in a rectification column,
  e) Collecting a product stream having a purity in ethanol of about 96 v %,
characterized in that the rectification column comprises at least one dividing wall.

The present invention further relates to use of dividing wall in distillation column in an ethanol purification process, in particular to separate ethanol from impurities such as higher alcohols. Further preferably, the invention relates to use of dividing wall in distillation column in an ethanol purification process to separate ethanol from water and from impurities such as higher alcohols. It has been found that the ethanol yield of a distillation column comprising a dividing wall is higher than the ethanol yield of the same column without dividing wall. In particular the invention relates to the use of dividing wall in a rectification column in an ethanol production process. The use of dividing wall column improves the separation of ethanol and higher alcohols. Thus the present invention relates to the use of dividing wall column in ethanol purification process to increase the ethanol yield of the process.

The invention will be further illustrated in following examples.

EXAMPLES

The ethanol content is measured with DMA 5000 from Anton Paar, at 20° C. and expressed in volume % (v %).

The amount of higher alcohols is measured by gas chromatography: Gas Chromatographer (GC), mainframe (injector and detectors FID and ECD) with software Agilent 7890, DB-WAX column.

Example 1

Use of Dividing Wall in a Potable Rectification Column and Separate Propanol Pump From Feed Side of the Wall to the Other Side of the Wall The rectification column is fed with a stream of 43750 kg/hr comprising a mixture of 14.6 vol % ethanol, 85.4 vol % water, and fusel (comprising 752 mg/l AA (i.e. mg/l AA of feed stream) iso-amyl alcohol (3-methyl-1-butanol), 302 mg/l AA 1-propanol, 396 mg/l AA iso-butanol (2-methyl-propan-1-ol), 13 mg/l AA 1-butanol).

The column has a top pressure of 2.5 bar absolute and pressure drop of 0.36 bar and consists of 75 trays in total. Feed tray is tray 16 (counting vertically from lower part to higher part). The dividing wall consists of 10 trays, from 1 tray below the feed tray to 8 trays above the feed tray. The liquid split over the two sides of the wall is 0.82/0.18, while the vapour split is 0.80/0.20. The reboiler has a positive duty of 10000 kW.

On the feed side of the wall a draw-off stream of propanol is taken (by means of a pump) from tray 18 and sent to the other side of the wall where it enters at tray 20 with a flow of 500 kg/hr.

On the outlet side of the wall 2 draw-offs are used, called propanol and fusel draw-off. Location of fusil draw-off is tray 17 with a flow of 200 kg/hr. Location of propanol draw-off is tray 23 (counting vertically from lower part to higher part) with a flow of 100 kg/hr.

The process results in a composition of product stream comprising 96.4 v % ethanol, without impurities (i.e. below detection limit of GC, i.e. <0.5 mg/l AA).

The process also results in a composition of propanol draw-off comprising 84.5 v % ethanol, 15.5 v % water, 3036 mg/l AA iso-amyl alcohol (3-methyl-1-butanol), 19202 mg/l AA 1-propanol, 17374 mg/l AA iso-butanol (2-methylpropan-1-ol), 281 mg/l AA 1-butanol.

The process also results in a composition of fusel draw-off comprising 36.7 v % ethanol, 63.3 v % water, 192255 mg/l AA iso-amyl alcohol (3-methyl-1-butanol), 49504 mg/l AA 1-propanol, 180106 mg/l AA iso-butanol (2-methylpropan-1-ol), and 5336 mg/l AA 1-butanol.

Example 2

Traditional Potable Rectification Without Dividing Wall Technology and Without a Propanol Pump The rectification column is fed with a stream of 43750 kg/hr comprising a mixture of 14.6 v % ethanol, 85.4 v % water, and fusel (comprising 752 mg/l AA (i.e. mg/l AA of feed stream) iso-amyl alcohol (3-methyl-1-butanol), 302 mg/l AA 1-propanol, 396 mg/l AA iso-butanol (2-methylpropan-1-ol), 13 mg/l AA 1-butanol).

The column has a top pressure of 2.5 bar absolute and pressure drop of 0.36 bar and consists of 75 trays in total. Feed tray is tray 16 (counting vertically from lower part to higher part). The reboiler has a positive duty of 10000 kW.

Two draw-offs are used, called propanol and fusel draw-off. Location of fusel draw-off is tray 16 with a flow of 405 kg/hr. Location of propanol draw-off is tray 17 (counting vertically from lower part to higher part) with a flow of 530 kg/hr.

This process results in a composition of main high quality draw-off comprising 96.4 v % ethanol, without impurities (i.e. below detection limit of GC, i.e. <0.5 mg/l AA).

The process also results in a composition of propanol draw-off comprising 49.3 v % ethanol, 50.7 v % water, 14824 mg/l AA iso-amyl alcohol (3-methyl-1-butanol), 6101 mg/l AA 1-propanol, 7817 mg/l AA iso-butanol (2-methylpropan-1-ol), 271 mg/l AA 1-butanol.

The process also results in a composition of fusel draw-off comprising 17.0 v % ethanol, 83.0 v % water, 9800 mg/l AA iso-amyl alcohol (3-methyl-1-butanol), 2971 mg/l AA 1-propanol, 5200 mg/l AA iso-butanol (2-methylpropan-1-ol), and 111 mg/l AA 1-butanol.

What is claimed is:

1. A process for the purification of ethanol comprising the steps of:
    a) Distilling an aqueous feed stream comprising water, ethanol in an amount below its azeotropic concentration, and 1 to 25,000 mg/l Absolute Alcohol (AA) higher alcohols comprising propanol and/or fusel alcohols in a distillation column comprising at least one dividing wall;
    b) Collecting propanol building up on a feed side of the dividing wall and feeding said propanol into the column at an outlet side of the dividing wall; and
    c) Collecting a stream having a higher purity in ethanol compared to the feed stream.

2. The process of claim 1 further comprising collecting one or more streams having a higher purity in higher alcohols, compared to the feed stream.

3. The process of claim 1 wherein the feed stream comprises at least 5 v % ethanol.

4. The process of claim 1 wherein the feed stream comprises from 100 to 25000 mg/l AA of higher alcohols.

5. The process of claim 1 comprising collecting a stream having a higher concentration in propanol and a stream having a higher concentration in fusel alcohols compared to the feed stream.

6. The process of claim 1 wherein the distillation column comprising the at least one dividing wall is a rectification column.

7. The process of claim 1 wherein the feed stream is coming from an alcoholic yeast fermentation process.

8. The process of claim 1 further comprising collecting fusel alcohols building up on the feed side of the dividing wall and feeding said fusel alcohols into the column at the outlet side of the dividing wall.

9. The process of claim 1 wherein the feed stream comprises 10 to 95 v % water.

10. The process of claim 1 wherein the stream collected in step c) has a purity in ethanol of from 60 to 98 v %.

11. A process for the purification of ethanol comprising the steps of:
    a) Distilling an aqueous feed stream in a distillation column comprising at least one dividing wall, the aqueous feed having 10 to 90 v % water, ethanol in an amount below its azeotropic concentration, and 1 to 25,000 mg/l Absolute Alcohol (AA) of higher alcohols comprising propanol and/or fusel alcohols;
    b) Collecting propanol and/or fusel alcohols building up on a feed side of the dividing wall and feeding said propanol and/or fusel alcohols into the column at an outlet side of the dividing wall; and
    c) Collecting a stream having a higher purity in ethanol compared to the feed stream, said purity being 60 to 98 v %.

* * * * *